United States Patent
Pedragosa-Moreau et al.

(10) Patent No.: US 9,476,071 B2
(45) Date of Patent: Oct. 25, 2016

(54) PROCESS FOR THE ENZYMATIC SYNTHESIS OF (7S)-3,4-DIMETHOXYBICYCLO[4.2.0]OCTA-1,3,5-TRIENE-7-CARBOXYLIC ACID AND APPLICATION IN THE SYNTHESIS OF IVABRADINE AND SALTS THEREOF

(71) Applicant: LES LABORATOIRES SERVIER, Suresnes (FR)

(72) Inventors: Sandrine Pedragosa-Moreau, Orleans (FR); François Lefoulon, Orleans (FR)

(73) Assignee: LES LABORATOIRES SERVIER, Suresnes (FR)

( * ) Notice: Subject to any disclaimer, the term of this patent is extended or adjusted under 35 U.S.C. 154(b) by 233 days.

(21) Appl. No.: 14/190,702

(22) Filed: Feb. 26, 2014

(65) Prior Publication Data
US 2014/0242644 A1 Aug. 28, 2014

(30) Foreign Application Priority Data
Feb. 28, 2013 (FR) ..................... 13 51785

(51) Int. Cl.
| | | |
|---|---|---|
| C07C 51/08 | (2006.01) | |
| C12P 41/00 | (2006.01) | |
| C12P 7/40 | (2006.01) | |
| C07C 62/34 | (2006.01) | |
| C07D 223/16 | (2006.01) | |
| C12N 9/78 | (2006.01) | |

(52) U.S. Cl.
CPC ............... *C12P 7/40* (2013.01); *C07C 51/08* (2013.01); *C07C 62/34* (2013.01); *C07D 223/16* (2013.01); *C12P 41/006* (2013.01); *C12Y 305/05001* (2013.01); *C07C 2102/06* (2013.01); *Y02P 20/52* (2015.11)

(58) Field of Classification Search
CPC ... C07C 2102/06; C07C 51/08; C07C 62/34; C07D 223/16; C12P 41/006; C12P 7/40; C12Y 305/05001
See application file for complete search history.

(56) References Cited

U.S. PATENT DOCUMENTS

| | | | |
|---|---|---|---|
| 2003/0157672 A1 | 8/2003 | Ress-Loschke | |
| 2008/0265206 A1 | 10/2008 | Kesseler | |
| 2009/0130726 A1* | 5/2009 | Wells ............... | C12P 13/002 435/128 |

FOREIGN PATENT DOCUMENTS

WO WO 2011/138625 11/2011

OTHER PUBLICATIONS

Luo et al., Appl. Biochem. Biotechnol. 160:393-400, 2010.*
Luo et al., GenBank accession No. ABO46008, Nov. 5, 2009.*
Alison J. Hoyle, et al., Enzyme and Microbial Technology, vol. 23, No. 7-8, p. 475-482, Nov. 1, 1998.
French Preliminary Search Report for FR1351785 of Oct. 15, 2013.
Gradley Michelle L. et al., Archives of Microbiology, vol. 161, No. 3, p. 246-251, Mar. 1, 1994.
Wikipedia, "Protein Production" (https://en.wikipedia.org/wiki/Protein_production).

* cited by examiner

*Primary Examiner* — Delia Ramirez
(74) *Attorney, Agent, or Firm* — Hueschen and Sage

(57) ABSTRACT

Process for the enzymatic synthesis of the compound of formula (I):

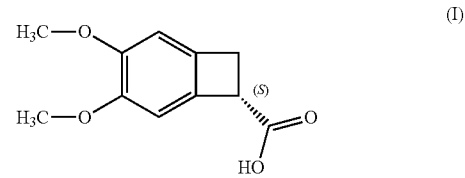

comprising enantioselective enzymatic hydrolysis of the nitrile of formula (IV):

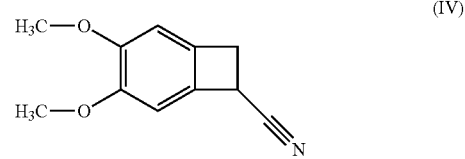

using the nitrilase of *Rhodococcus rhodochrous* of EMBL accession number EF467367.1, and the application of such a process in the synthesis of ivabradine and addition salts thereof with a pharmaceutically acceptable acid.

15 Claims, 2 Drawing Sheets

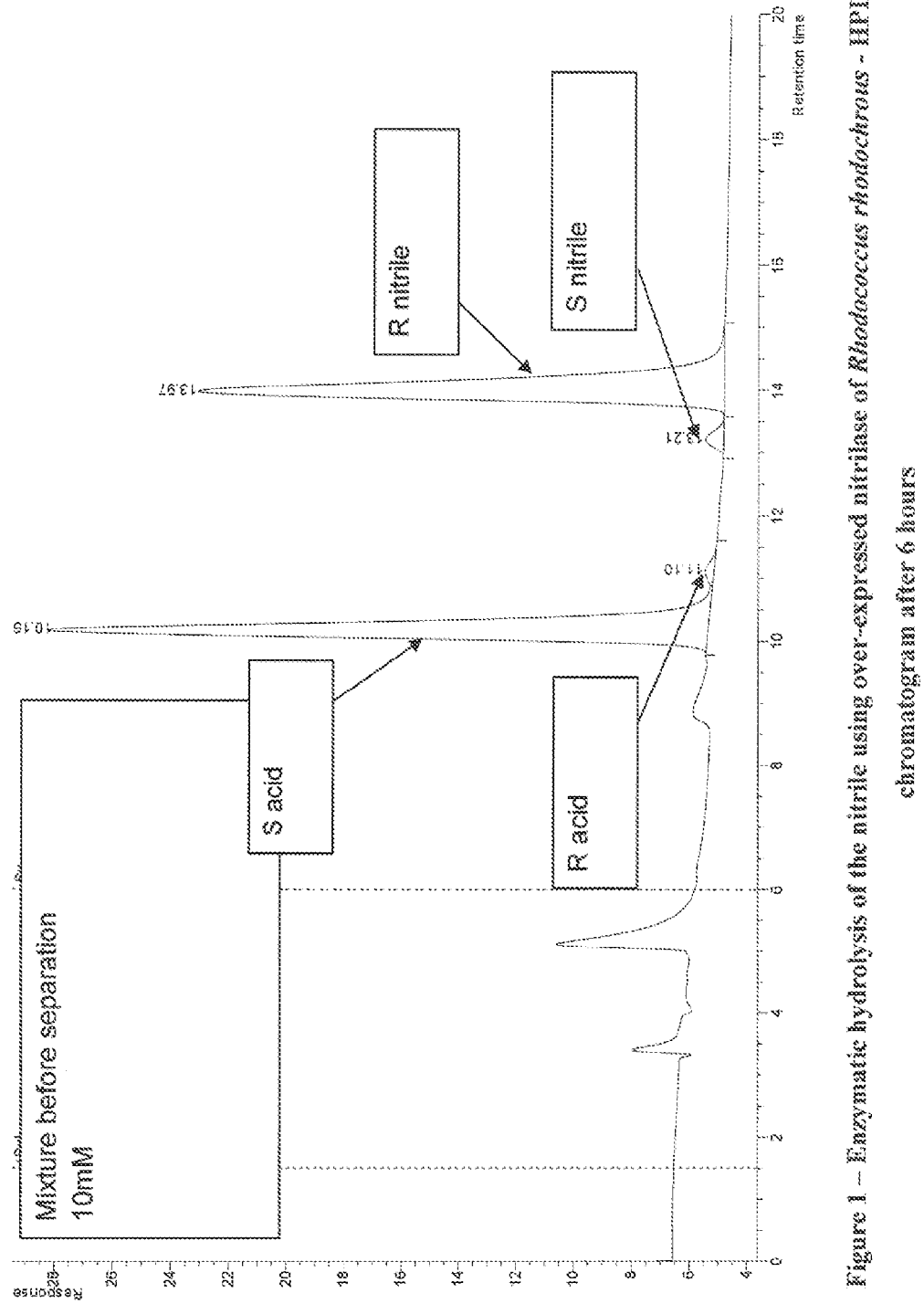
Figure 1 – Enzymatic hydrolysis of the nitrile using over-expressed nitrilase of *Rhodococcus rhodochrous* – HPLC chromatogram after 6 hours

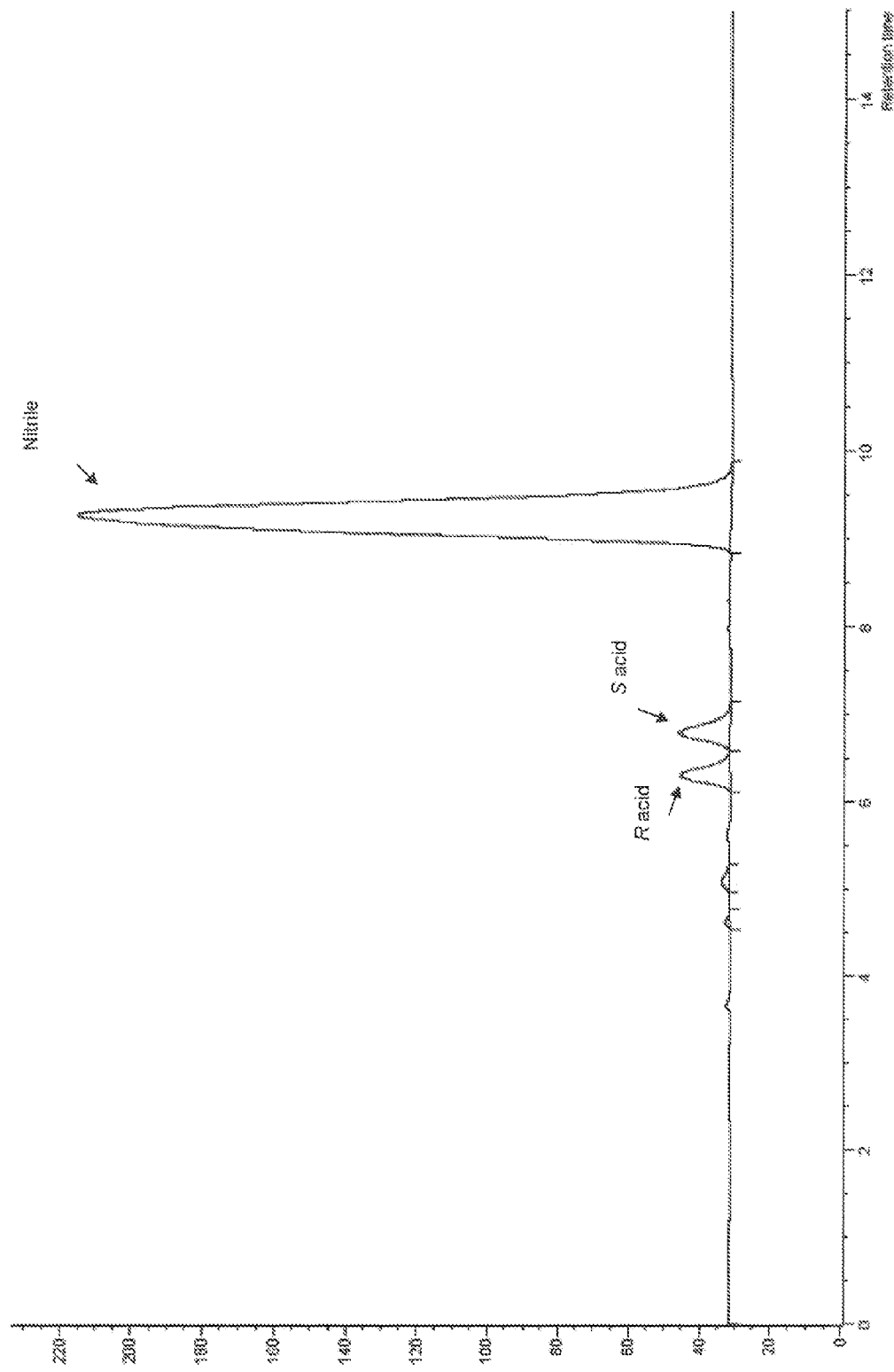
Figure 2 – Enzymatic hydrolysis of the nitrile using NIT 115 HPLC chromatogram after 5 hours

PROCESS FOR THE ENZYMATIC SYNTHESIS OF (7S)-3,4-DIMETHOXYBICYCLO[4.2.0]OCTA-1,3,5-TRIENE-7-CARBOXYLIC ACID AND APPLICATION IN THE SYNTHESIS OF IVABRADINE AND SALTS THEREOF

The present invention relates to a process for the enzymatic synthesis of the compound of formula (I):

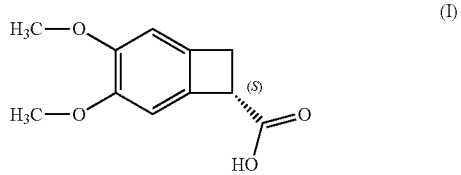

(I)

and to the application thereof in the synthesis of ivabradine of formula (II):

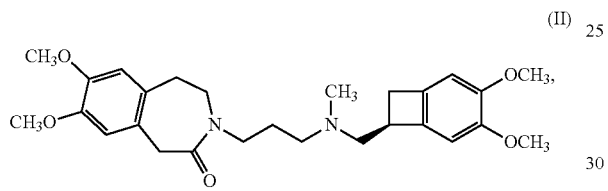

(II)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
its addition salts with a pharmaceutically acceptable acid and their hydrates.

Ivabradine, and addition salts thereof with a pharmaceutically acceptable acid, and more especially the hydrochloride thereof, have very valuable pharmacological and therapeutic properties, especially bradycardic properties, which render those compounds useful in the treatment or prevention of various clinical conditions of myocardial ischaemia, such as angina pectoris, myocardial infarction and associated rhythm disorders, as well as in various pathologies involving rhythm disorders, especially supraventricular rhythm disorders, and in heart failure.

The preparation and therapeutic use of ivabradine and addition salts thereof with a pharmaceutically acceptable acid, and more especially the hydrochloride thereof, have been described in European patent specification EP 0 534 859.

That patent specification describes the synthesis of ivabradine hydrochloride starting from the compound of formula (III), (7S)-1-(3,4-dimethoxybicyclo[4.2.0]octa-1,3,5-trien-7-yl) N-methyl methanamine:

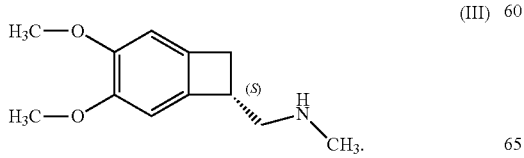

(III)

The compound of formula (III) is a key intermediate in the synthesis of ivabradine and pharmaceutically acceptable salts thereof.

The prior art discloses several methods for obtaining the compound of formula (III).

Patent specification EP 0 534 859 describes synthesis of the compound of formula (III) by reduction of the nitrile of formula (IV):

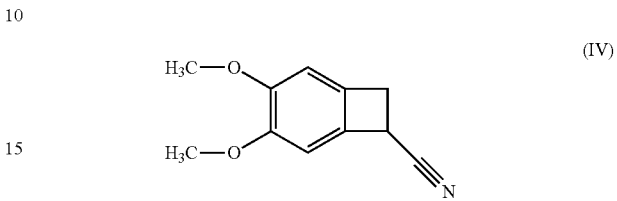

(IV)

by $BH_3$ in tetrahydrofuran, followed by addition of hydrochloric acid, to yield the hydrochloride of the racemic amine of formula (V):

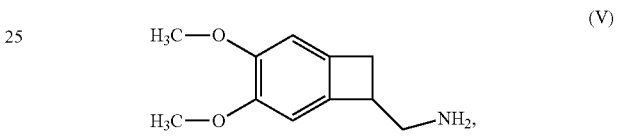

(V)

which is reacted with ethyl chloroformate to yield the carbamate of formula (VI):

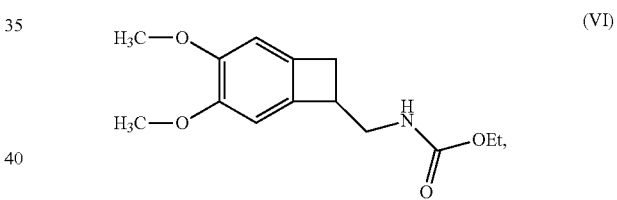

(VI)

the reduction of which, by $LiAlH_4$, yields the racemic methylated amine of formula (VII):

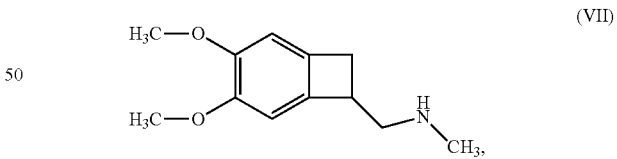

(VII)

the resolution of which, using camphorsulphonic acid, yields the compound of formula (III). That method has the disadvantage of yielding the compound of formula (III) in only a very low yield of 2 to 3% starting from the racemic nitrile of formula (IV).

That very low yield is due to the low yield (4 to 5%) of the step of resolution of the secondary amine of formula (VII).

Patent specification EP 2 166 004 describes obtaining the compound of formula (III) by optical resolution of the racemic nitrile of formula (IV) using chiral chromatography to yield the optically pure nitrile of formula (IX):

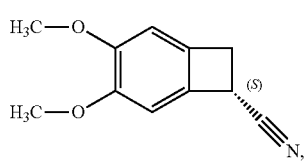

which is reduced using NaBH$_4$ or by hydrolytic hydrogen, to yield the primary amine of formula (VIII).

The primary amine can then be methylated using the same reaction sequence as above (conversion into the carbamate, and then reduction).

The compound of formula (III) can be obtained thereby in 5 steps starting from the racemic nitrile of formula (IV), in a yield of 45.6% for the resolution step.

Using hydrolytic nitrilase enzymes (EC 3.5.5.1 in the international classification of enzymes) seemed promising in order to allow the optically pure acid of formula (I) to be obtained directly starting from the racemic nitrile of formula (IV) and thereby to reduce the number of steps for obtaining the methylated amine of formula (III) starting from the racemic nitrile.

The nitrile of formula (X) has been described as a substrate of nitrilases from the NESK-1400 screening kit marketed by the company Almac:

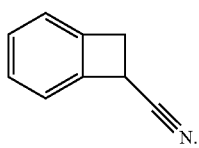

However, using these same nitrilases on the nitrile of formula (IV) (cf. Comparative Example A) showed them to have low activity with little selectivity, resulting in most cases in the simultaneous formation of amide (nitrile hydratase activity) and acid, which is difficult to exploit for the purposes of synthesis for obtaining intermediates in the synthesis of the compound of formula (III).

The problem of the present invention was accordingly to find a nitrilase allowing enantioselective synthesis of the optically pure acid of formula (I) starting from the racemic nitrile of formula (IV), whilst minimising the formation of amide.

The Applicant then found evidence of nitrilase activity in various whole micro-organisms with preferential formation of the acid of formula (I), of configuration S. Of the micro-organisms tested, only *Rhodococcus rhodocrous* allowed the (S) acid to be obtained with very good enantioselectivity, without formation of amide (cf. Comparative Example B).

This activity was improved by over-expression of the nitrilase.

Surprisingly, enzymatic hydrolysis using this over-expressed nitrilase is not enantioselective for the substrate of formula (X) (cf. Comparative Example C).

More specifically, the present invention relates to a process for the synthesis of the optically pure compound of formula (I):

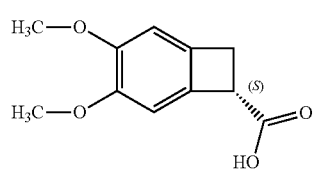

by enantioselective enzymatic hydrolysis of the racemic, or not optically pure, nitrile of formula (IV):

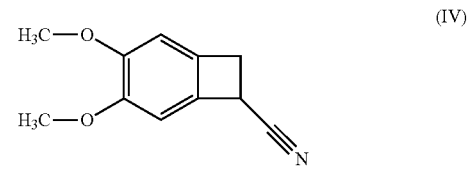

using the nitrilase of *Rhodococcus rhodocrous* NCIMB 11216 over-expressed in another organism having a competent biological system, such as a bacteria, a yeast or a fungus, in a mixture of an organic solvent and an aqueous solution having a pH from 5 to 10, preferably a buffer having a pH from 5 to 10, at a concentration from 1 to 500 g/L, preferably from 2 g to 100 g of nitrile of formula (IV) per liter of solvent mixture, at an E/S ratio of from 1/1 to 1/100, at a temperature from 25° C. to 40° C.

In accordance with an aspect of the invention, the nitrilase is over-expressed in a bacteria comprising a rearranged plasmid, such as *Escherichia coli*, preferably *E. coli* BL21 (DE3), *E. coli* BL21(DE3)pLysS, *E. coli* BL21star(DE3) or *E. coli* JM9(DE3).

In accordance with an aspect of the invention, the organic solvent is a solvent completely or partially miscible with water, such as dimethyl sulphoxide, DMF, acetone, acetonitrile, an alcohol such as ethanol or isopropanol, or an ether such as THF or MTBE.

In accordance with another aspect of the invention, the organic solvent is not miscible with water, for example a hydrocarbon such as heptane or octane.

The aqueous solution is preferably a buffer solution having a pH of about 7.

In accordance with an aspect of the invention, the bacteria over-expressing the nitrilase are used directly in the process, in the form of a bacterial slurry or lyophilisate.

The E/S ratio is preferably from 1/1 to 1/10 in the case of a bacterial slurry, and from 1/10 to 1/20 in the case of a lyophilisate.

In accordance with another aspect of the invention, the nitrilase is used in the form of purified enzyme.

The schema for enzymatic hydrolysis according to the invention is as follows:

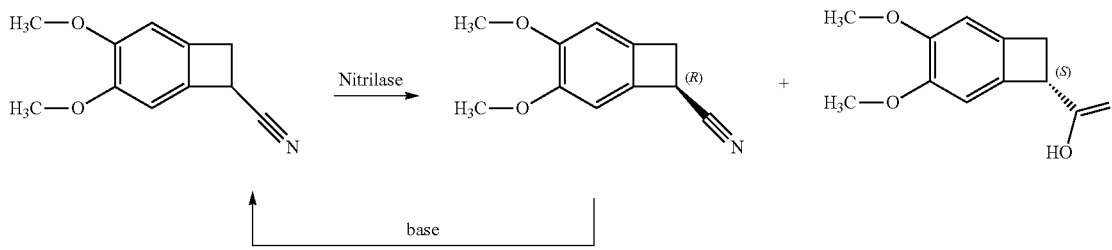

Advantageously, the nitrile of configuration (R), the secondary reaction product, is racemised by the action of an organic base such as DBU or of a mineral base such as sodium hydroxide, potassium hydroxide, potassium carbonate or sodium carbonate in order to be recycled into the enzymatic hydrolysis process.

When the racemisation step is carried out in situ, the process according to the invention is a dynamic kinetic resolution (DKR) process which makes it possible to obtain the S acid of formula (I) with an ee of more than 98%.

The acid of formula (I) is preferably isolated from the reaction medium after one or more enzymatic hydrolysis cycles.

BRIEF DESCRIPTION OF THE DRAWINGS

FIG. 1 shows the HPLC chromatogram after 6 hours for the enzymatic hydrolysis of the nitrile using over-expressed nitrilase of *Rhodococcus rhodochrous*.

FIG. 2 shows the HPLC chromatogram after 5 hours for the enzymatic hydrolysis of the nitrile using NIT 115.

DEFINITIONS

An optically pure compound is understood to be a compound having an enantiomeric excess greater than or equal to 90%.

A nitrile which is not optically pure is understood to be a nitrile having an enantiomeric excess less than 90%.

A racemic nitrile is understood to be a nitrile in the form of a mixture of two enantiomers in a ratio of from 55:45 to 45:55.

Enantioselective hydrolysis of a racemic, or not optically pure, nitrile is understood to be preferential hydrolysis of one of the enantiomers of the mixture.

A competent biological system is understood to refer to (a) biological species (host cells) whose genetic material has been modified by genetic recombination, making it/them capable of producing a recombinant protein of interest. An expression vector (plasmid) constructed for that purpose allows the DNA coding for the gene of interest to be transferred into the host cell, which may thereby efficiently (over-)express the functional protein.

Another aspect of the invention relates to a process for the synthesis of the compound of formula (III) in only two steps, starting from the optically pure acid of formula (I), which is converted into the optically pure amide of formula (XI):

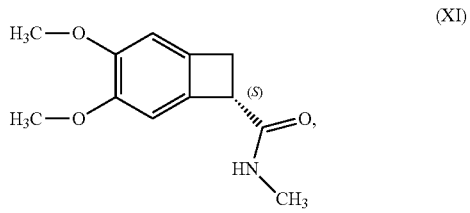

the reduction of which, preferably by $BH_3$, $NaBH_4$ or $LiAlH_4$, yields the compound of formula (III).

The compound of formula (III) is subsequently either coupled with a compound of formula (XII):

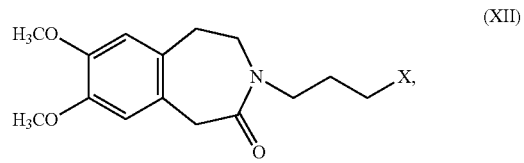

wherein X represents a halogen atom, preferably an iodine atom, or subjected to a reductive amination reaction with a compound of formula (XIII) in the presence of a reducing agent:

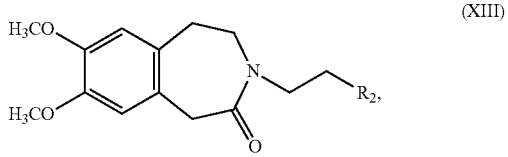

wherein $R_2$ represents a group selected from CHO and $CHR_3R_4$, wherein $R_3$ and $R_4$ each represent a linear or branched $(C_1$-$C_6)$alkoxy group or form, together with the carbon atom carrying them, a 1,3-dioxane, 1,3-dioxolane or 1,3-dioxepane ring, to yield ivabradine, which is then converted into an addition salt with a pharmaceutically acceptable acid, said salt being in anhydrous or hydrate form.

The compound of formula (III) may also be used in the reductive amination reaction in the form of its addition salt with a pharmaceutically acceptable acid, preferably its hydrochloride. In that case, ivabradine is obtained directly in the form of the hydrochloride.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

Among the reducing agents that may be used for the reductive amination reaction between the compound of formula (III) and the compound of formula (XIII) there may be mentioned, without implying any limitation, hydride donor compounds such as sodium triacetoxyborohydride or sodium cyanoborohydride, and dihydrogen in the presence of a catalyst such as palladium, platinum, nickel, ruthenium, rhodium or a compound thereof, especially on a support or in the form of oxides.

The preferred reducing agent for the reductive amination reaction between the compound of formula (III) and the compound of formula (XIII) is dihydrogen catalysed by palladium-on-carbon.

The Examples hereinbelow illustrate the invention.

ABBREVIATIONS

TFA TriFluoroAcetic acid
TLC Thin-Layer Chromatography
DBU DiazaBicycloUndecene
DKR Dynamic Kinetic Resolution
DMF DiMethylFormamide
DMSO DiMethyl SulphOxide
OD Optical density
E Enantio selectivity coefficient
ee enantiomeric excess
eq molar equivalent
HPLC High Performance Liquid Chromatography
IPTG IsoPropyl β-D-1-ThioGalactopyranoside
LB Lysogeny Broth culture medium
MeOH Methanol
MTBE Methyl Tert-Butyl Ether
op optical or enantiomeric purity
E/S ratio Enzyme/Substrate ratio, expressed in g/g
NMR Nuclear Magnetic Resonance (spectroscopy)
MS Mass Spectrometry
THF TetraHydroFuran
TMS TetraMethylSilane

EXAMPLE 1

(7S)-3,4-Dimethoxybicyclo[4.2.0]octa-1,3,5-triene-7-carboxylic acid

Over-Expression of the Nitrilase:

The nitrilase protein of *Rhodococcus rhodochrous* NCIMB 11216 is described in protein and genome databases. The sequence of the sought gene is listed under the identifier SVA (Sequence Version Archive) "EF467367" in the ENA (European Nucleotide Archive) of EMBL-Bank. This sequence corresponds to the reference "A4LA85" in the UniProtKB/TrEMBL database.

The production strain *E. coli* BL21(DE3), transformed with the expression vector pET28a-Nit1, was used.

The nitrilase over-expression protocol is described in *Applied Biochemistry and Biotechnology* 2010, Vol 160(2), pp 393-400.

The cells thereby transformed are either used directly in the form of a bacterial slurry or are lyophilised before use. Enzymatic Hydrolysis Using the Over-Expressed Nitrilase.

The cells transformed according to the above protocol are stirred at a concentration of $5.6 \times 10^9$ cells/mL (1 mL of culture at OD=1 (600 nm) corresponds to $1 \cdot 10^9$ bacteria and about 10 mg of bacterial slurry or 1.5 mg of lyophilisate).

To a solution of 250 mL of phosphate buffer $KH_2PO_4$/$Na_2HPO_4$ 1/15 M at pH 7 there are added 1 g of lyophilisate of *E. coli* and 500 mg (c=2 g/L, 10 mM) of 3,4-dimethoxybicyclo[4.2.0]octa-1,3,5-triene-7-carbonitrile in 2% of DMSO (5 mL).

The reaction mixture is maintained at 30° C., with rotary stirring at 220 rpm, for 6 hours.

The reaction is monitored by chiral-phase HPLC under conditions allowing the enantiomeric excess of the acid and nitrile to be determined:
Chiralpak IB Column
90% n-hexane 10% 2-PrOH+0.1% TFA
1 mL/min 30° C. 288 nm

|  | % nitrile | ee (nitrile) | % acid | ee (acid) | conversion | E |
|---|---|---|---|---|---|---|
| 6 hours | 49.9 | 94 | 50.1 | 97 | 0.49 | >100 |

*enantioselectivity coefficient $E = \ln[1 - c(1 + ee(acid))]/\ln[1 - c(1 - ee(acid))]$ The chiral-phase HPLC chromatogram after 6 hours is shown in FIG. 1.

After reacting for 6 hours, the reaction mixture is acidified with 1M HCl in order to obtain a highly acid pH (pH 2) and is then extracted with 2×100 mL of dichloromethane. The organic phase is drawn off. A second extraction using toluene (2×100 mL) makes it possible to recover all the product remaining in the aqueous phase. The organic phases are washed with saturated NaCl solution and then dried using anhydrous magnesium sulphate. After evaporation of the solvents, the crude product is obtained, which is purified by flash chromatography on a silica column under the following conditions:
Column type: 80 g SiOH Macherey-Nagel
Material and method: Reveleris
Eluant: Isocratic (cyclohexane+1% acetic acid/ethyl acetate+1% acetic acid 75/25)
Detection: UV 288 nm
Flow rate: 60 ml/min
Result:
Nitrile (R): yield 36% (179 mg), ee (R): 96%
Acid (S): yield 39% (246 mg), ee (S): 96%

EXAMPLE 2

3,4-Dimethoxybicyclo[4.2.0]octa-1,3,5-triene-7-carbonitrile by racemisation of the (R) nitrile Transfer 100 mg of (R)-(3,4-dimethoxybicyclo[4.2.0] octa-1,3,5-trien-7-yl)nitrile (0.53 mmol), 5 mL of isopropanol and 121 mg of DBU (1.5 eq.) to a flask provided with a condenser and a magnetic stirrer. Heat for 2 hours at 65° C. and then allow to return to ambient temperature. Filter to obtain the title compound.

EXAMPLE 3

(7S)-3,4-Dimethoxy-N-methylbicyclo[4.2.0]octa-1,3,5-triene-7-carboxamide

Suspend the (7S)-3,4-dimethoxybicyclo[4.2.0]octa-1,3,5-triene-7-carboxylic acid obtained in Example 1 (300 mg) in THF (3 ml) at ambient temperature and then add triethylamine (200 µl). Ethyl chloroformate (150 µl) is added slowly to the mixture. The reaction mixture precipitates (mixture I).

In another flask, methylamine, as a 2M solution in THF (2.25 ml), is stirred with water (1 ml) and triethylamine (300 µl). Stirring is maintained for 20 minutes and then the resulting mixture is added to mixture I and stirred at ambient temperature overnight.

The reaction mixture is then evaporated and purified by preparative HPLC.

(7S)-3,4-Dimethoxy-N-methylbicyclo[4.2.0]octa-1,3,5-triene-7-carboxamide is obtained in a yield of 60%.

$^1$H NMR (DMSO-d6, ppm/TMS)=2.61 (m; 3H); 3.16 (m; 2H); 3.71 (s; 6H); 4.05 (m; 1H); 6.78 (s; 1H); 6.81 (s; 1H); 7.78 (br s; 1H).

EXAMPLE 4

(7S)-3,4-Dimethoxybicyclo[4.2.0]octa-1,3,5-trien-7-yl]N-methyl methanamine

Suspend the (7S)-3,4-dimethoxy-N-methylbicyclo[4.2.0]octa-1,3,5-triene-7-carboxamide obtained in Example 3 (450 mg) in tetrahydrofuran (20 mL) and then slowly add 1.6 mL of 2M LiAlH$_4$ solution in tetrahydrofuran to the reaction mixture at ambient temperature. Marked evolution of gas is observed and the reaction mixture becomes clear. Heat the reaction mixture at reflux for 30 minutes.

After returning to ambient temperature, hydrolyse and then extract with ethyl acetate. Dry over MgSO$_4$ and then evaporate. The residue obtained is purified by preparative HPLC (eluant: water/acetonitrile/trifluoroacetic acid from 98/2/0.2 to 20/80/0.2) over 30 minutes to yield the title product in a yield of 46%.

$^1$H NMR (DMSO-d6, ppm/TMS)=2.60 (m; 3H); 2.85 (m; 1H); 3.15 (m; 1H); 3.25 (dd; 1H); 3.30 (m; 1H); 3.62 (m; 1H); 3.70 (s; 6H); 6.82 (s; 1H); 6.89 (s; 1H); 8.48 (br s; 1H).

EXAMPLE 5

(7S)-3,4-Dimethoxybicyclo[4.2.0]octa-1,3,5-trien-7-yl]N-methyl methanamine hydrochloride 20 mL of a molar solution of BH$_3$ in tetrahydrofuran are added, at ambient temperature, to a mixture of 2.2 g (10 mmol) of (7S)-3,4-dimethoxy-N-methylbicyclo[4.2.0]octa-1,3,5-triene-7-carboxamide obtained in Example 3 in 45 mL of tetrahydrofuran. After stirring for 1 hour, 10 mL of the solution of BH$_3$ in tetrahydrofuran are added. After stirring overnight at ambient temperature, 20 mL of ethanol are added dropwise and the mixture is stirred until no more gas is evolved (about 1 hour). 20 mL of hydrochloric acid solution in ethanol are then added dropwise. After stirring for 4 hours, the precipitate obtained (1.2 g of the title product) is filtered off. The filtrate is concentrated and an additional 0.65 g of the title product is obtained by rendering it solid in an 80/20 mixture of ethyl acetate/ethanol.

The two precipitates are combined to yield 1.85 g of the title product (yield: 77%).

EXAMPLE 6

Ivabradine hydrochloride

Load 5.5 kg of 3-[2-(1,3-dioxolan-2-yl)ethyl]-7,8-dimethoxy-1,3-dihydro-2H-3-benzazepin-2-one, 27.5 liters of ethanol and 550 g of palladium-on-carbon into an autoclave. Purge with nitrogen and then with hydrogen, heat to 55° C., and then hydrogenate at that temperature under a pressure of 5 bars until the theoretical amount of hydrogen has been absorbed.

Then return to ambient temperature and depressurise the autoclave.

Then add 4 kg of (7S)-3,4-dimethoxybicyclo[4.2.0]octa-1,3,5-trien-7-yl]N-methyl methanamine hydrochloride, 11 liters of ethanol, 5.5 liters of water and 1 kg of palladium-on-carbon.

Purge with nitrogen and then with hydrogen, heat to 85° C., and then hydrogenate at that temperature under a pressure of 30 bars until the theoretical amount of hydrogen has been absorbed.

Then bring back to ambient temperature, purge the autoclave and then filter the reaction mixture; distil off the solvents and then isolate the ivabradine hydrochloride by crystallisation from a toluene/1-methyl-2-pyrrolidinone mixture.

Ivabradine hydrochloride is thereby obtained in a yield of 85% and with a chemical purity greater than 99%.

COMPARATIVE EXAMPLE A

Screening Commercial Nitrilases for Enzymatic Hydrolysis of 3,4-dimethoxybicyclo[4.2.0]octa-1,3,5-triene-7-carbonitrile Weigh the nitrilase being studied (15 mg), in the form of a lyophilisate, into a tube and then add 4 ml of 0.1M KH$_2$PO$_4$ buffer pH=7 and 3,4-dimethoxybicyclo[4.2.0]octa-1,3,5-triene-7-carbonitrile (20 mg) dissolved in 100 µl of DMSO.

Place in an incubator at 28° C. and 220 rpm.

The conversion rate was measured by HPLC after 24 hours and 72 hours.

The nitrilases NIT 101, NIT 102, NIT 103, NIT 104, NIT 105, NIT 106, NIT 108, NIT 109, NIT 111, NIT 112 and NIT 113 (Almac) do not hydrolyse the nitrile after 24 hours (no formation of acid or of amide).

The results obtained with the nitrilases NIT 107, NIT 110, NIT 114 and NIT 115 (Almac) are collated in the Table below:

| Nitrilase | 72 hours | | |
| --- | --- | --- | --- |
| | Amide | Acid | Nitrile |
| NIT 107 | 23% | 16% | 61% |
| NIT 110 | 24% | 15% | 61% |
| NIT 114 | 21% | 22% | 57% |
| NIT 115 | 7% | 47% | 46% |

Analytical Conditions:

Phenomenex LUNA HST 50*3 column     C18(2) 2.5 µm
0% to 100% B over 8 mins    0.8 ml/min    40° C.
A (1000 water + 25 ACN + 1 TFA)
B (1000 ACN + 25 water + 1 TFA)

The nitrilase NIT 115 was then used in another study to determine if hydrolysis of the nitrile is enantioselective.

The nitrilase NIT 115 (12 mg; Almac) was used in 6 mL [2 mg/mL] of buffer.

3,4-Dimethoxybicyclo[4.2.0]octa-1,3,5-triene-7-carbonitrile was added to reach a final concentration of 4 mg/mL thereof.

Enantioselectivity was measured by HPLC using the following analytical conditions:
Chiralpak IC 250*4.6 column
30% absolute ethanol+0.1% TFA+70% heptane+0.1% TFA
1 ml/min 30° C. 288 nm
Note: Under these conditions, the enantiomers of the acid are separated but not those of the nitrile.

The chromatogram obtained after reacting for 5 hours is shown in FIG. 2.

Conclusion

No enantioselectivity is observed.

COMPARATIVE EXAMPLE B

Screening Nitrilases of Bacterial and Fungal Strains for Enzymatic Hydrolysis of 3,4-dimethoxybicyclo[4.2.0]octa-1,3,5-triene-7-carbonitrile A study using a number of bacterial inducers (propionitrile, benzonitrile, 4-bromobenzonitrile) showed that propionitrile provided the best induction of nitrilase activity with 3,4-dimethoxybicyclo[4.2.0]octa-1,3,5-triene-7-carbonitrile.

The bacterial strains were induced with propionitrile at 72 mM for 72 hours, and the cells were taken up in 50 mL (twice concentrated, conc. 10 mg of cells per ml) of 0.1M phosphate buffer $KH_2PO_4/K_2HPO_4$ pH=7.3 and 3,4-dimethoxybicyclo[4.2.0]octa-1,3,5-triene-7-carbonitrile was added at a concentration of 10 mM in 2% of DMSO v/v$_{final}$.

The fungal strains were induced with valeronitrile.

All the reaction mixtures were stirred at 220 rpm at 30° C. in the case of the bacteria and at 27° C. in the case of the fungi and monitored for 96 hours by reverse-phase HPLC and by chiral-phase HPLC according to the methods described below:

Reverse-Phase Analysis

| Phenomenex LUNA HST 50*3 column | | C18(2) 2.5 μm |
|---|---|---|
| 0% B to 100% B over 8 mins | 0.8 ml/min | 40° C. |
| A (1000 water + 25 ACN + 1 TFA) | | |
| B (1000 ACN + 25 water + 1 TFA) | | |

Chiral-Phase Analysis

Chiralpak IC 250*4.6 column
30% absolute ethanol+0.1% TFA+70% heptane+0.1% TFA
1 ml/min 30° C. 288 nm The results obtained are collated in the Table below:

| MICRO-ORGANISMS | % compounds formed after 96 hours | | |
|---|---|---|---|
| | Residual nitrile | amide | acid |
| Rhodococcus erythropolis NCIMB11215 | 23 | 42 | 35 (S) |
| Rhodococcus rhodochrous NCIMB11216 | 65 | / | 35 (S) |
| Rhodococcus rhodochrous NCIMB11273 | 100 | / | / |
| Rhodococcus rhodnii NCIMB11279 | 100 | / | / |
| Aspergillus niger BO | 95 | / | <5 |
| Aspergillus alliaceus NRRL 315 | 95 | / | <5 |
| Cunninghamella elegans NRRL 1392 | 95 | / | <5 |
| Rhizopus nigricans NRRL 1477 | 95 | / | <5 |
| Absidia cylindrospora MMP 1569 | 95 | / | <5 |
| Mortierella isabellina NRRL 1757 | 95 | / | <5 |
| Mucor plumbeus ATCC 4740 | 95 | / | <5 |
| Beauveria bassiana ATCC 7159 | 86 | / | 14 |
| Stibella fimetaria CBS 548-84 | 100 | / | / |
| Stibella fimetaria CBS 511-67 | 100 | / | / |
| Stibella fimetaria CBS 294-81 | 100 | / | / |

COMPARATIVE EXAMPLE C

Enzymatic Hydrolysis of bicyclo[4.2.0]octa-1,3,5-triene-7-carbonitrile Using the Over-Expressed Nitrilase of Rhodococcus rhodochrous NCIMB 11216

Plating on LB+agar+kanamycin, static incubation at 37° C. for 24 hours (strain 11216 of nitrilase of recombinant E. coli).

Preculture in 5 ml of LB+kanamycin (50 mg/1), incubation at 37° C., 180 rpm overnight. Culture: transfer 50 ml of LB and 500 μl of preculture to non-baffled 250-ml Erlenmeyer flasks, incubation at 28° C., 160 rpm until the OD is equal to 0.6 (i.e. about 4 hours).

Induction with IPTG (0.5 mM), incubation at 17° C., 160 rpm overnight (17 hours).

Activity test: centrifuge the cultures at 4° C., 6000 rpm for 20 minutes, resuspend the slurry in 10 ml of 0.1M phosphate buffer pH 7. Add bicyclo[4.2.0]octa-1,3,5-triene-7-carbonitrile (10 mM)+2% ethanol. Incubate at 220 rpm, 30° C.

Note: If the culture is more than 50 ml when centrifuging, take off 50 ml and carry out the activity test using a slurry of 50 ml of culture.

Hydrolysis monitoring by chiral chromatography: at 45 mins and 2 hours.

Column: Phenomenex® LUNA HST 50*3 C18(2) 2.5 μm
Eluant: A+B (from 0% to 100% B over 8 mins)
A: 1000 water+25 ACN+1 TFA
B: 1000 ACN+25 water+1 TFA
0.8 ml/min—40° C.—UV 210 nm
Results:

| Time | Nitrile | Carboxylic acid |
|---|---|---|
| 45 minutes | 50% | 50% |
| 2 hours | 0% | 100% |

Monitoring by chiral chromatography shows that the reaction is not enantioselective.

The invention claimed is:

1. A process for the synthesis of an optically pure compound of formula (I):

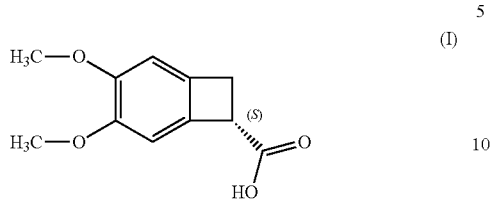

comprising enantioselective enzymatic hydrolysis of the racemic, or not optically pure, nitrile of formula (IV):

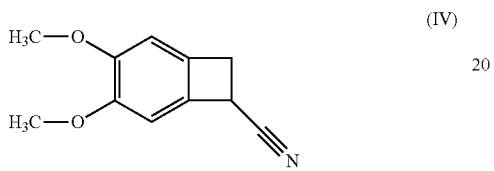

using the nitrilase of *Rhodococcus rhodochrous* of EMBL accession number EF467367.1, having SEQ ID NO: 1, expressed in a competent biological system, in a mixture of an organic solvent and an aqueous solution having a pH from 5 to 10,
at a concentration from 1 to 500 g of nitrile of formula (IV) per liter of solvent mixture,
at an Enzyme/Substrate (E/S) ratio of from 1/1 to 1/100,
at a temperature from 25° C. to 40° C.

2. The process according to claim 1, wherein the competent biological system is a bacteria comprising a plasmid which encodes the nitrilase.

3. The process according to claim 2, wherein the bacteria expressing the nitrilase are used directly, in the form of a bacterial slurry or lyophilisate.

4. The process according to claim 1, wherein the organic solvent is selected from dimethyl sulphoxide, dimethylformamide (DMF), acetone, acetonitrile, ethanol, isopropanol, tetrahydrofuran (THF) and methyl tert-butyl ether (MTBE).

5. The process according to claim 1, wherein the secondary product of the reaction, the nitrile of configuration (R):

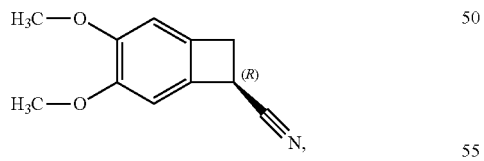

is racemised by the action of a base to form the racemic nitrile of formula (IV) which is recycled into the enzymatic hydrolysis process.

6. The process according to claim 5, wherein the base is diazabicycloundecene (DBU).

7. The process according to claim 5, wherein the racemisation step is carried out in situ.

8. The process according to claim 5, wherein the acid of formula (I) is isolated after one or more enzymatic hydrolysis cycles.

9. A process for the synthesis of the compound of formula (III):

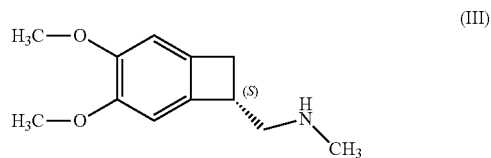

or an addition salt thereof,
wherein the process comprises the following steps:
(a) hydrolyzing a nitrile of formula (IV):

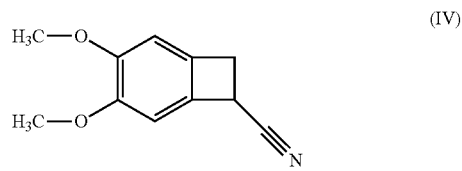

under enantioselective enzymatic hydrolysis conditions using the nitrilase of *Rhodococcus rhodochrous* of EMBL accession number EF467367.1, having SEQ ID NO: 1, expressed in a competent biological system,
in a mixture of an organic solvent and an aqueous solution having a pH from 5 to 10, at a concentration from 1 to 500 g of nitrile of formula (IV) per liter of solvent mixture,
at an E/S ratio of from 1/1 to 1/100,
at a temperature from 25° C. to 40° C.
to obtain an optically pure acid of formula (I):

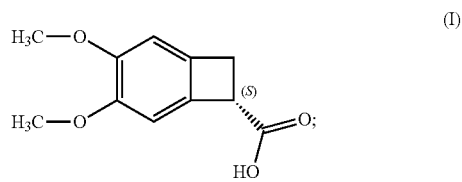

(b) converting the optically pure acid of formula (I) into an optically pure amide of formula (XI):

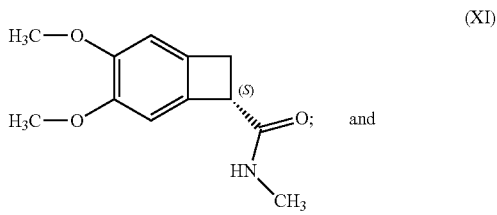

(c) reducing the optically pure amide of formula (XI) to obtain the compound of formula (III), wherein the compound of formula (III) may be optionally converted to an addition salt with a pharmaceutically acceptable acid.

10. The process according to claim 9, wherein the reduction of the compound of formula (XI) to form the compound of formula (III) is carried out by $BH_3$, $NaBH_4$ or $LiAlH_4$.

11. A process for the synthesis of ivabradine, or an addition salt thereof, wherein
the process comprises the following steps:
(a) hydrolyzing a nitrile of formula (IV):

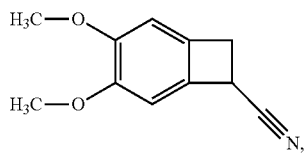

(IV)

under enantioselective enzymatic hydrolysis conditions using the nitrilase of *Rhodococcus rhodochrous* of EMBL accession number EF467367.1, having SEQ ID NO: 1, expressed in a competent biological system,
in a mixture of an organic solvent and an aqueous solution having a pH from 5 to 10,
at a concentration from 1 to 500 g of nitrile of formula (IV) per liter of solvent mixture,
at an E/S ratio of from 1/1 to 1/100,
at a temperature from 25° C. to 40° C.
to obtain an optically pure acid of formula (I):

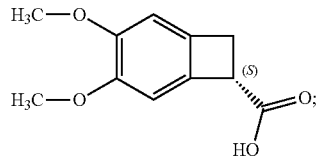

(I)

(b) converting the optically pure acid of formula (I) into an optically pure amide of formula (XI):

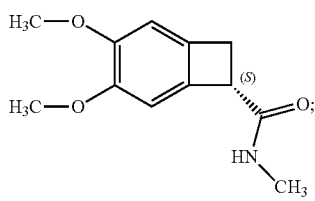

(XI)

(c) reducing the optically pure amide of formula (XI) to obtain a compound of formula (III):

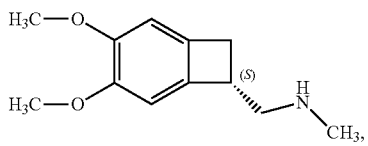

(III)

wherein the compound of formula (III) may be optionally converted to an addition salt with a pharmaceutically acceptable acid;

(d) coupling the compound of formula (III), or acid addition salt thereof, with a compound of formula (XII):

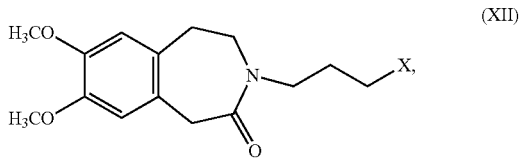

(XII)

wherein X represents a halogen atom,
or subjecting the compound of formula (III), or acid addition salt thereof, to a reductive amination reaction with a compound of formula (XIII) in the presence of a reducing agent:

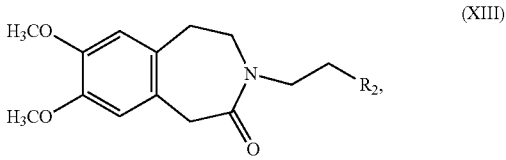

(XIII)

wherein $R_2$ is a group selected from CHO and $CHR_3R_4$,
wherein $R_3$ and $R_4$ each represent a linear or branched $(C_1\text{-}C_6)$alkoxy group or $R_3$ and $R_4$, together with the carbon atom carrying them, form a 1,3-dioxane, 1,3-dioxolane or 1,3-dioxepane ring,
to yield ivabradine; and (e) converting ivabradine into an addition salt with a pharmaceutically acceptable acid in anhydrous or hydrate form.

12. The process according to claim 11, wherein X is an iodine atom.

13. The process according to claim 11, wherein the addition salt of the compound of formula (III) is used in the reductive amination reaction, wherein the addition salt is a hydrochloride salt, and wherein an ivabradine hydrochloride salt is produced.

14. The process according to claim 11, wherein the reductive amination reaction with the compound of formula (XIII) is carried out in the presence of dihydrogen catalysed by palladium-on-carbon.

15. The process according to claim 13, wherein the reductive amination reaction with the compound of formula (XIII) is carried out in the presence of dihydrogen catalysed by palladium-on-carbon.

* * * * *

SEQUENCE LISTING

<160> NUMBER OF SEQ ID NOS: 1

<210> SEQ ID NO 1
<211> LENGTH: 366
<212> TYPE: PRT
<213> ORGANISM: Rhodococcus rhodochrous

<400> SEQUENCE: 1

```
Met Val Glu Tyr Thr Asn Thr Phe Lys Val Ala Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
        35                  40                  45

Val Phe Ile Pro Gly Tyr Pro Tyr His Ile Trp Val Asp Ser Pro Leu
    50                  55                  60

Ala Gly Met Ala Lys Phe Ala Val Arg Tyr His Glu Asn Ser Leu Thr
65                  70                  75                  80

Met Asp Ser Pro His Val Gln Arg Leu Leu Asp Ala Ala Arg Asp His
                85                  90                  95

Asn Ile Ala Val Val Gly Ile Ser Glu Arg Asp Gly Gly Ser Leu
            100                 105                 110

Tyr Met Thr Gln Leu Ile Ile Asp Ala Asp Gly Gln Leu Val Ala Arg
            115                 120                 125

Arg Arg Lys Leu Lys Pro Thr His Val Glu Arg Ser Val Tyr Gly Glu
        130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Glu Asn
225                 230                 235                 240

Glu Glu Gln Arg Lys Leu Ile Gly Arg Gly Gly Phe Ala Arg Ile
                245                 250                 255

Ile Gly Pro Asp Gly Arg Asp Leu Ala Thr Pro Leu Ala Glu Asp Glu
            260                 265                 270

Glu Gly Ile Leu Tyr Ala Asp Ile Asp Leu Ser Ala Ile Thr Leu Ala
        275                 280                 285

Lys Gln Ala Ala Asp Pro Val Gly His Tyr Ser Arg Pro Asp Val Leu
    290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Phe Gly Ala Leu
                325                 330                 335

Asp Gly Val Arg Glu Leu Asn Gly Ala Asp Glu Gln Arg Ala Leu Pro
            340                 345                 350

Ser Thr His Ser Asp Glu Thr Asp Arg Ala Thr Ala Ser Ile
        355                 360                 365
```